United States Patent
Jynge et al.

(10) Patent No.: US 10,869,938 B2
(45) Date of Patent: Dec. 22, 2020

(54) MAGNETIC RESONANCE IMAGING

(75) Inventors: Per Jynge, Trondheim (NO); Arne Skjold, Trondheim (NO); Henrik W. Larsson, Glostrup (DK)

(73) Assignee: 1C TARGETS AS, Oslo (NO)

( * ) Notice: Subject to any disclaimer, the term of this patent is extended or adjusted under 35 U.S.C. 154(b) by 1540 days.

(21) Appl. No.: 12/522,931

(22) PCT Filed: Jan. 18, 2008

(86) PCT No.: PCT/GB2008/000191
§ 371 (c)(1),
(2), (4) Date: Jan. 4, 2010

(87) PCT Pub. No.: WO2008/087445
PCT Pub. Date: Jul. 24, 2008

(65) Prior Publication Data
US 2010/0166667 A1    Jul. 1, 2010

(30) Foreign Application Priority Data

Jan. 18, 2007 (GB) .................................. 0700999.6

(51) Int. Cl.
*A61K 49/10* (2006.01)
*A61P 9/00* (2006.01)

(52) U.S. Cl.
CPC ............... *A61K 49/103* (2013.01); *A61P 9/00* (2018.01)

(58) Field of Classification Search
None
See application file for complete search history.

(56) References Cited

U.S. PATENT DOCUMENTS 6,482,800 B1 * 11/2002 Rodgers et al. ............. 514/13.3

FOREIGN PATENT DOCUMENTS

WO    99/01162    1/1999

OTHER PUBLICATIONS

Waller et al. Serial magnetic resonance imaging of microvascular remodeling in the infarcted rat heart. 2001 Circulation 103: 1564-1569.*
International Search Report for PCT/GB2008/000191, dated Sep. 16, 2008.
Written Opinion of the International Searching Authority for PCT/GB2008/000191, dated Sep. 16, 2008.
Nordhoy et al., "Intracellular Manganese Ions Provide Strong T1 Relaxation in Rat Myocardium", Magnetic Resonance in Medicine, 52: 506-514 (2004).
Brurok et al., "Effects of MnDPDP, DPDP and $MnCl_2$ on Cardiac Energy Metabolism and Manganese Accumulation", Invstigative Radiology vol. 32, No. 4, 1997, Lippincott-Raven Publishers, pp. 205-211.
Skjold et al., "Relaxation Enhancing Properties of MnDPDP in Human Myocardium", Journal of Magnetic Resonance Imaging, 2004, Wiley=Liss, Inc., pp. 948-952.
Borkowski et al, "Cation dyshomeostasis and cariomyoctye necrosis: the Flectenstein hypothesis revisited", European Heart Journal (2011)32, 1846-1853.

* cited by examiner

*Primary Examiner* — Jennifer Lamberski
(74) *Attorney, Agent, or Firm* — Birch, Stewart, Kolasch & Birch, LLP

(57) ABSTRACT

A method of determining the amount of intracellular manganese in the myocardium of an individual pre-administered with a manganese contrast agent, or a pharmaceutically acceptable salt thereof, comprising subjecting, the individual to a MRI procedure to assess the signal intensity (SI) of images, or more preferably the longitudinal relaxation rate, $R_1$ throughout the myocardium.

32 Claims, 6 Drawing Sheets

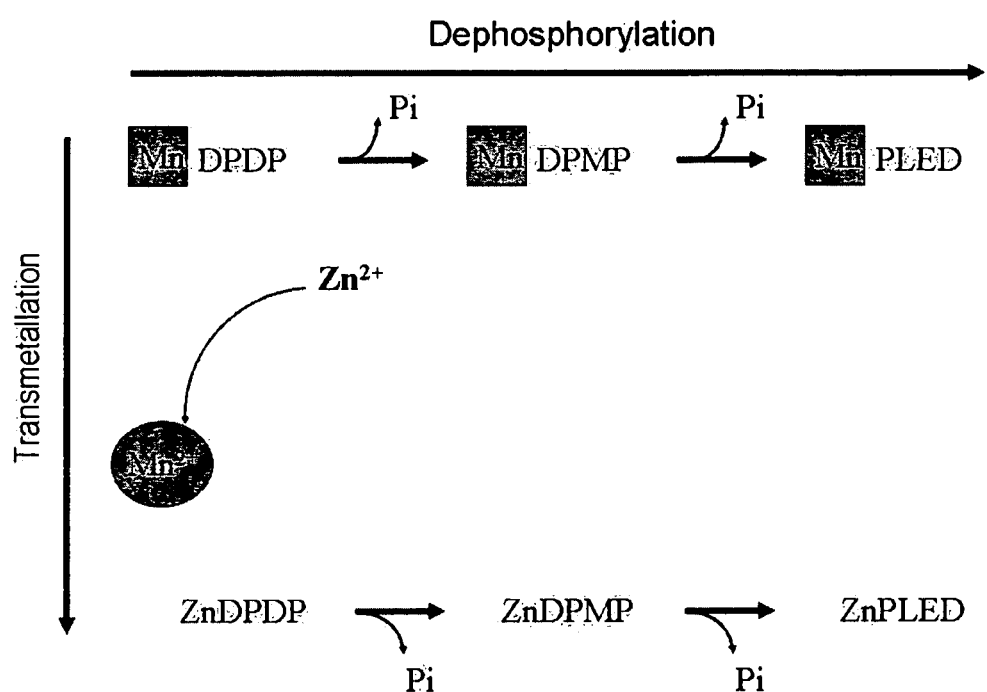
Figure 1 Plasma kinetics and metabolism of MnDPDP after *iv.* infusion of Teslascan.

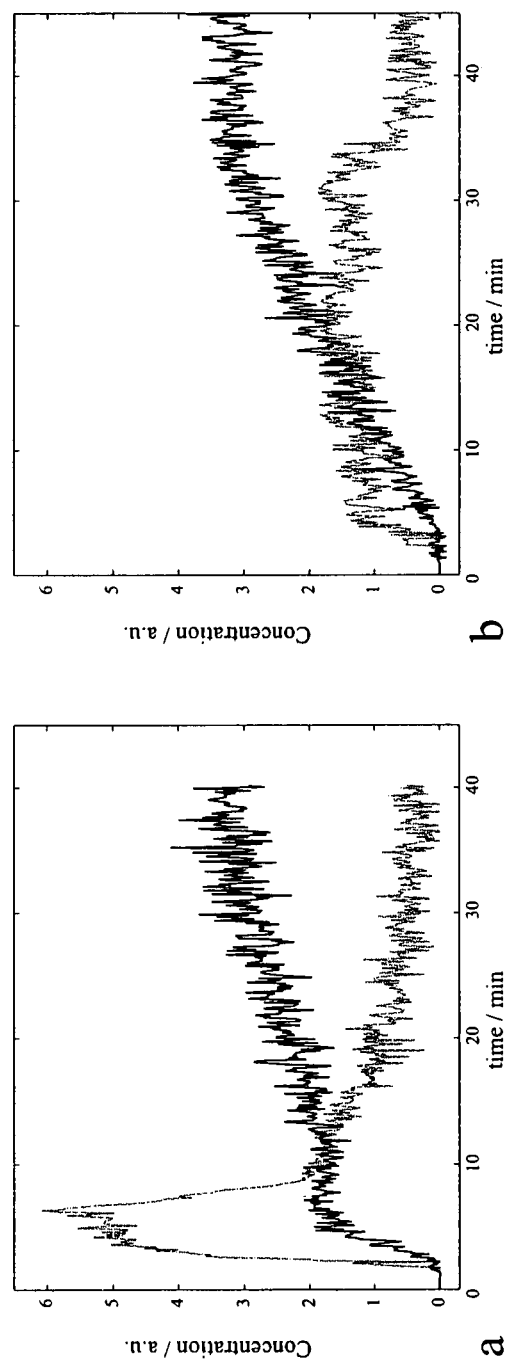
Figure 2. MR kinetics in terms of changes in SI (arbitrary "concentration" units) in LV chamber blood (grey) and in LV myocardium (black) during and following: a) 5 min iv. infusion of Teslascan; and b) 30 min iv. infusion of Teslascan. Applied dose 5 μmol/kgbw. Results obtained in adult and healthy human voluteers.

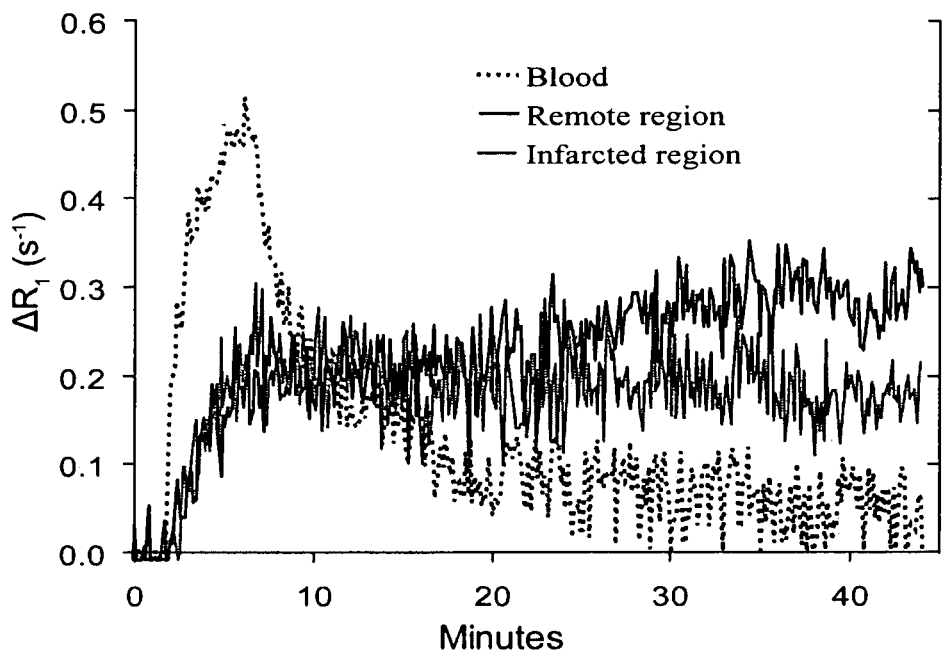

Figure 3. Manganese uptake kinetics assessed by $R_1$ mesurements in a patient with a persistent myocardial infarction in the LV lateral wall. Teslascan 5 µmol/kg bw was infused over 5 minutes. Observe that in the early 5 min period there is also a consistent uptake in the infarcted-fibrotic area, but there is no (late) uptake thereafter. There is both an early and a late uptake in the remote and normal myocardium.

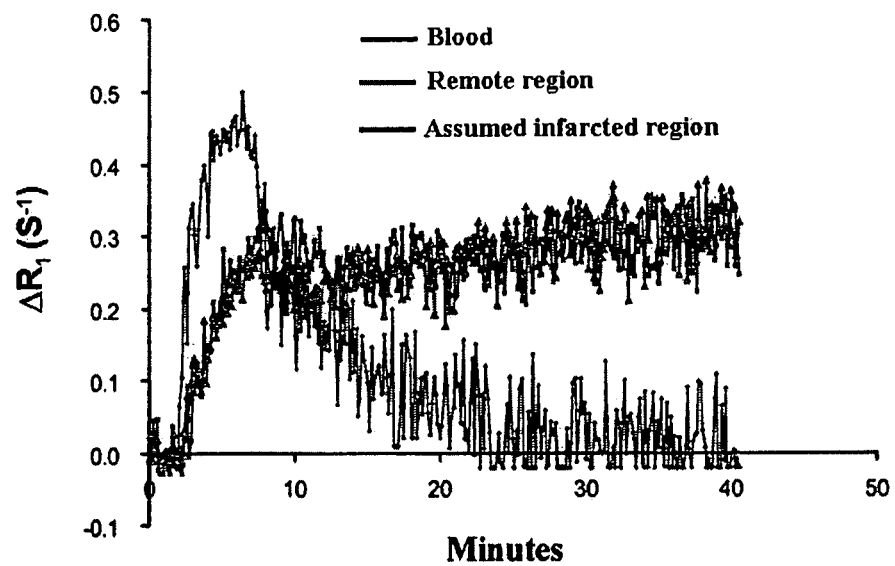
Figure 4. Manganese uptake kinetics assessed by $R_1$ mesurements in a patient with an assumed infarction but with myocardial salvage at PCI.. Teslascan 5 µmol/kg bw was infused over 5 minutes. Observe that in both the early 5 min period and thereafter there is an identical uptake in the assumed infarcted area as in the remote and normal area.

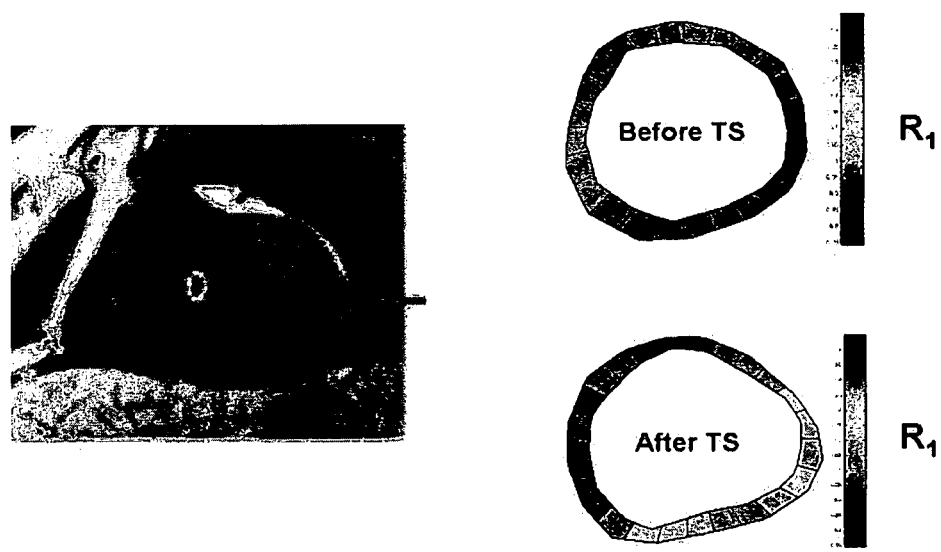
Figure 5. Patient with persistent infarct indicated by arrow in the left picture. The diagram of the LV ventricle presents $R_1$ values distributed in the LV slice covering the infarcted area. Observe the great heterogeneity that appears about 40 min after infusion of Teslascan (TS).

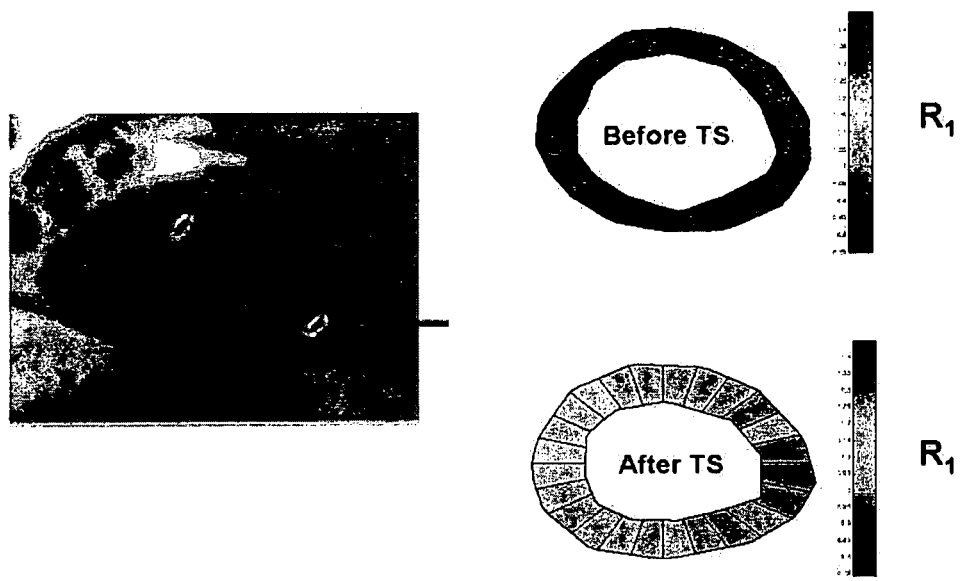

Figure 6. Patient with suspected infarction indicated by arrow in the left picture but with myocardial salvage on revascularization by PCI. Diagram of the LV ventricle presents $R_1$ values distributed in the LV slice covering the assumed but noninfarcted area. Observe the great homogeneity that is present before and about 40 min after infusion of Teslascan (TS) and the major and uniform elevation of $R_1$ values

MAGNETIC RESONANCE IMAGING

This application is the U.S. national phase of International Application No. PCT/GB2008/000191, filed 18 Jan. 2008, which designated the U.S. and claims priority to Great Britain Application No. 0700999.6, filed 18 Jan. 2007, the entire contents of each of which are hereby incorporated by reference.

The present invention relates to magnetic resonance imaging (MRI) and in particular to methods and uses of MRI employing manganese contrast agents to determine tissue viability/function at a graded level and thereby to detect cardiac remodelling.

Ischemic heart disease (IHD) caused by atherosclerosis, thrombosis and/or occlusion of arteries still accounts for the majority of deaths in western countries. The most common potentially fatal event associated with IHD is acute myocardial infarction (AMI), arrhythmias and heart failure during or following AMI.

In recent years, the treatment of AMI has improved greatly and many individuals now survive an AMI due to the availability of rapid revascularisation with drugs and/or percutaneous intervention. Sadly, however, a significant number of individuals receiving such treatment, as well as individuals with even small infarctions, subsequently develop remodelling of the left ventricle and heart failure which has a high level of mortality and morbidity. Remodelling encompasses both structural, metabolic and functional changes in the infarcted (now scarred) region, in the neighbouring border zone and to different degrees throughout the entire ventricle. These heterogenous changes predispose an individual both to life threatening arrhythmias and to failure of the cardiac pump, i.e. heart failure. There is therefore a need for methods for identifying and monitoring remodelling of the myocardium so that the necessary action, be it pharmacological or surgical, can be taken before a fatal event occurs.

A major difficulty to be overcome in developing methods for detecting remodelling of the myocardium is differentiating between myocardial perfusion and myocardial viability. On a cellular level, viability requires that myocardial blood flow be sufficient to sustain non-impeded oxidative metabolism, thus viability is inherently linked to perfusion. Conversely, however, perfusion does not always indicate viability as coronary arteries reopened spontaneously or by revascularisation treatment may supply blood flow to an area of non viable tissue. Methods for detecting perfusion are therefore of limited utility in identifying or monitoring cardiac remodelling.

Perfusion may, for example, be assessed by fast bolus tracking MRI of an intravenously injected extracellular Gd-containing contrast agent such as Gd-DTPA or Gd-DTPA-BMA. The determination of viability, however, depends on the accumulation of the Gd-based contrast agent in infarcted tissue and can only be seen by waiting 10-20 minutes after the initial administration of contrast agent and repeating the MRI. A major drawback of this technique is that dead or non-functioning tissue is imaged. Thus information on viable mycocardium is only obtained indirectly.

Manganese enhanced MRI is another technique that can be used to image the myocardium. This technique is based on the fact that manganese ions enter cells via $Ca^{2+}$ channels and therefore accumulate in living cells. The accumulated manganese leads to increased signal intensity (SI) in images. More importantly, the accumulated manganese also leads to a reduction in longitudinal relaxation time ($T_1$) and consequently to an increase in the longitudinal relaxation rate, $R_1$ ($R_1=1/T_1$) of these cells versus the cells lacking manganese. A contributing factor to $R_1$ enhancement by manganese is strong protein binding. Hence by MRI a picture of living versus necrotic tissue can be captured.

WO99/01162, for example, describes use of various manganese complexes for detecting myocardial ischemia, and in particular for distinguishing viable myocardial tissue from infarcted tissue by MRI. To identify viable tissue, a manganese complex is administered to a body and, within a time period of from 3 to 6 hours, the body is imaged by MRI. Viable cells take up the manganese complex, whereas it is hypothesised that in infarcted tissue the manganese rapidly distributes therethrough by perfusion but is not retained by cells. The delay of 3 to 6 hours after administration to begin imaging is thus specifically designed to ensure that the manganese has effectively cleared from non viable tissue and hence a contrast with viable cells can be detected.

The methods described in WO99/001162 therefore enables viable and infarcted tissue to be distinguished This method, however, require a waiting period of 3 to 6 hours following administration of the contrast agent and commencing of imaging and hence is costly in terms of patient and healthcare time. Moreover there are no means provided for assessing different levels of viability or function. In other words, by the methods of WO99/001162 tissue can only be categorised as viable or non viable, i.e. as a "yes" or "no" and not as a quantifiable, graded viability phenomenon. US2002/0090341 has a similar related disclosure.

WO 2006/028379 discloses a magnetic resonance method for assessing myocardial viability wherein T1 and T2 relativities and water diffusion for intracellular and extracellular water compartments are detected separately. This method is essentially an improved means for carrying out known methods of assessing viability (e.g. as described in WO 99/01162). Again, the results offer a simple viability yes/no not a quantifiable, graded viability phenomenon.

There is a clear distinction between simple viability where a basic yes/no conclusion is offered and graded viability leading to a diagnosis of cardiac remodelling as clinical concepts. Simple viability in ischemic heart disease means the ability of myocardial tissue to survive, i.e. to live or die, during an episode of threatening acute myocardial infarction (AMI).

In contrast, cardiac remodelling is a description of differentiated and compensatory changes taking place throughout the entire wall of the left ventricle (and through the entire heart) after an AMI, i.e. compensatory changes due to a local loss of viable tissue and thus of local function.

The sick heart after AMI is characterized by heterogeneity with a mixture of: dead cells, live but poorly functioning (downregulated) cells, normal cells, and supernormal cells to compensate for the functional loss or impairment of others. Typically the region most remote (opposite in a transaxial slice in the patent examples which follow) becomes thicker than normal (exentric hypertrophy) and contracts more strongly. This represents true remodelling, a situation or condition which does not ensure normal cardiac function but signifies heterogeneity and heralds the onset of heart failure with gradual loss of an integrated pump function. Furthermore, remodelling also disposes for changes in electrophysiology of the heart and may correlate with lethal arrhythmias.

Without wishing to be limited by theory, it is believed that remodelling caused by an AMI is a process taking place in the entire ventricle, i.e. also outside the infarction and including both intermediate and remote areas.

A patient demonstrating a relatively large $R_1$ gradient between the infarct- and peri-infarct areas and the remote area soon after AMI would be at a high risk of developing life-threatening congestive heart failure and arrhythmias at a later stage. Such a patient should be put on aggressive pharmacological treatment. Repeated examinations with, for example, Mn enhancement and $R_1$ assessments is thus a new modality to monitor the remodelling process. Such a method should solve two important medical problems: namely to predict who will develop congestive heart failure or not; and who will respond to treatment by drugs or revascularisation (PCI, coronary bypass surgery.)

To facilitate cardiac remodelling there is a need for techniques which enable myocardial viability/function to be determined more rapidly so that changes therein can be monitored over time. Moreover, there is a need for techniques that can distinguish different levels of viability/function and not just offer the yes/no conclusion offered by the prior art. It has now surprisingly been found that this can be achieved by use of manganese based contrast agents in a particular MRI regime.

The manganese (II) chelate of N,N-bis-(pyridoxal-5-phosphate)-ethylenediamine-N,N'-diacetic acid (MnDPDP) is a well known contrast agent for use in MRI. MnDPDP administered to the body is metabolised in plasma in two ways as shown in FIG. 1. In a first pathway, MnDPDP undergoes transmetallation with Zn in plasma to release $Mn^{2+}$ ions that are rapidly taken up by cells via $Ca^{2+}$ channels. In a second pathway MnDPDP is believed to undergo enzymatic degradation by plasma phosphatases to its monophosphate derivative, MnDPMP and to its non-phosphorylated derivative, MnPLED. These biomarkers may then enter cells as intact molecules and/or undergo transmetallation to release $Mn^{2+}$ ions which can enter cells via $Ca^{2+}$ channels as described above.

The rate of accumulation of healthy myocardial cells was studied in J. Magnetic Resonance Imaging (2006, 24:1047-1055). In this study, healthy individuals were infused over 5 or 30 minutes with MnDPDP and the manganese accumulation or concentration in cells followed by MRI. The study reports that the 5 minute infusion of MnDPDP yields a biphasic curve for manganese tissue concentration versus time wherein there is an early, rapid $Mn^{2+}$ concentration increase and a later, slower $Mn^{2+}$ concentration increase whereas with the 30 minute infusion the $Mn^{2+}$ concentration increased steadily. The total amount manganese accumulated was, however, constant. The graphs are shown in FIG. 2.

The present invention is based on the surprising finding that when a manganese contrast agent such as MnDPDP is administered to an unhealthy individual non viable tissue with scar proteins (e.g. collagen) rapidly take up or bind $Mn^{2+}$ for a short time after infusion of MnDPDP (like the initial phase of the above-described biphasic curve) but thereafter cease uptake. Viable cells can therefore be differentiated from non-viable cells by the presence of manganese therein. More significantly, the amount of intracellular manganese provides a quantitative measure of viability, i.e. of function. As the amount of manganese present in a cell is shown to be essentially proportional to the signal intensity (SI) and $R_1$ values determined by MRI, SI and/or $R_1$ measurements can be used to provide a quantitative measurement of intracellular manganese and tissue viability/function. This is particularly useful for detecting cardiac remodelling.

Thus, viewed from a first aspect the invention provides a method of determining the amount of intracellular manganese in the myocardium of an individual pre-administered with a manganese contrast agent, or a pharmaceutically acceptable salt thereof, comprising subjecting said individual to a MRI procedure to assess the signal intensity (SI) of images, or more preferably the longitudinal relaxation rate, $R_1$ throughout said myocardium.

Viewed from a further aspect the invention provides a method of determining myocardial tissue viability/function in an individual pre-administered with a manganese contrast agent, or a pharmaceutically acceptable salt thereof, said method comprising subjecting said individual to a MRI procedure to determine the amount of intracellular manganese in the myocardium of said individual, preferably by the method hereinbefore described.

Alternatively viewed the invention provides a method of determining myocardial tissue viability/function in an individual, said method comprising:
(i) administering a manganese contrast agent, or a pharmaceutically acceptable salt thereof, to said individual; and
(ii) subjecting said individual to a MRI procedure whereby to determine the amount of intracellular manganese in the myocardium of said individual, preferably by the method hereinbefore described.

In yet another view, the invention provides use of a manganese contrast agent, or a pharmaceutically acceptable salt thereof, in the manufacture of a composition for use in a method of determining myocardial tissue viability/function in an individual, wherein said method comprises:
(i) administering a manganese contrast agent, or a pharmaceutically acceptable salt thereof, to said individual; and
(ii) subjecting said individual to a MRI procedure whereby to determine the amount of intracellular manganese in the myocardium of said individual, preferably by the method hereinbefore described.

Viewed from a still further aspect the present invention provides a method of detecting cardiac remodelling in an individual, said method comprising:
(i) administering a manganese contrast agent, or a pharmaceutically acceptable salt thereof, to said individual; and
(ii) subjecting said individual to a MRI procedure whereby to determine myocardial tissue viability/function, preferably by determining the amount of intracellular manganese in the myocardium of said individual (e.g. by assessing the signal intensity (SI) of images, or more preferably the longitudinal relaxation rate, $R_1$ throughout said myocardium).

Alternatively viewed the invention provides use of a manganese contrast agent, or a pharmaceutically acceptable salt thereof, in the manufacture of a composition for use in a method of detecting cardiac remodelling in an individual, wherein said method comprises:
(i) administering a manganese contrast agent, or a pharmaceutically acceptable salt thereof, to said individual; and
(ii) subjecting said individual to a MRI procedure whereby to determine myocardial tissue viability/function, preferably by determining the amount of intracellular manganese in the myocardium of said individual (e.g. by assessing the signal intensity (SI) of images, or more preferably the longitudinal relaxation rate, $R_1$ throughout said myocardium).

Viewed from another aspect the invention provides a manganese contrast agent, or a pharmaceutically acceptable salt thereof, for use in a method of determining myocardial tissue viability/function in an individual, wherein said method comprises:
(i) administering a manganese contrast agent, or a pharmaceutically acceptable salt thereof, to said individual; and (ii) subjecting said individual to a MRI procedure whereby to determine the amount of intracellular manganese in the myocardium of said individual, preferably by the method hereinbefore described.

Viewed from another aspect the invention provides a manganese contrast agent, or a pharmaceutically acceptable salt thereof, for use in a method of detecting cardiac remodelling in an individual, wherein said method comprises:
(i) administering a manganese contrast agent, or a pharmaceutically acceptable salt thereof, to said individual; and
(ii) subjecting said individual to a MRI procedure whereby to determine myocardial tissue viability/function, preferably by determining the amount of intracellular manganese in the myocardium of said individual (e.g. by assessing the signal intensity (SI) of images, or more preferably the longitudinal relaxation rate, $R_1$ throughout said myocardium).

Preferred methods and uses of the invention for detecting cardiac remodelling, further comprise step (iii):
(iii) repeating steps (i) and (ii) and assessing whether any changes in myocardial tissue viability/function have occurred. Step (iii) may optionally be carried out after a period (e.g. days, weeks, months) of treatment.

By the term "determine the amount of manganese" is meant that a value on a quantitative or semi-quantitative scale (e.g. a quantitative scale) is attributed to the amount of intracellular manganese present. In other words a graded value on a scale is attributed to the amount of manganese present. This term does not therefore encompass determinations that simply yield a present or absent conclusion. The value obtained can therefore be correlated to the probability of tissue viability/function and hence to the presence of cardiac remodelling.

By the term "tissue viability" is meant the probability that the tissue will live and function in the normal manner. Critically therefore, the term "tissue viability" as used herein does not correspond to a simple yes/no conclusion but rather to a graded assessment of whether the tissue in question will function. Alternatively viewed therefore the term "tissue viability" might be considered to mean "tissue function", i.e. the probability that the tissue will live and function in the normal manner.

By the term "cardiac remodelling" is meant the changes in size, shape, metabolism and function of the heart after injury, especially to the left ventricle.

By the term "manganese contrast agent" is meant herein an agent which comprises at least one manganese atom or ion.

The use of manganese contrast agents in MRI is well known in the patent and scientific literature, e.g. as described in WO99/01162, the contents of which are incorporated herein by reference. All manganese contrast agents as described therein, and their pharmaceutically acceptable salts, are suitable for the uses and methods herein described.

The manganese contrast agent may be in the form of an ionic or more preferably a non-ionic complex. Especially preferred in the uses and methods of the invention are manganese chelate complexes, which may be bound to one or more carrier molecules.

Particularly preferred contrast agents are slow-release manganese contrast agents. These contrast agents retain manganese within their structure for some time after administration in vivo, e.g. until the contrast agent has reached the intravascular system. Preferred manganese ion releasing chelate complexes are those which dissociate in vivo to provide a release of manganese ions on passage through the heart. Conveniently, the manganese chelate may have a Ka value in the range of from $10^7$ to $10^{25}$, more preferably $10^9$ to $10^{24}$, yet more preferably $10^{10}$ to $10^{23}$, e.g. $10^{12}$ to $10^{22}$.

A wide range of suitable chelants and macromolecule bound chelants for manganese ions have been proposed. Dipyridoxyl based chelating agents have, for example, been described for use as MRI contrast agents. Manganese (II) chelates with dipyridoxyl chelating agents are particularly preferred for the uses and methods of the present invention.

Preferred for the uses and methods of the invention are manganese chelates of a compound of formula I and salts thereof

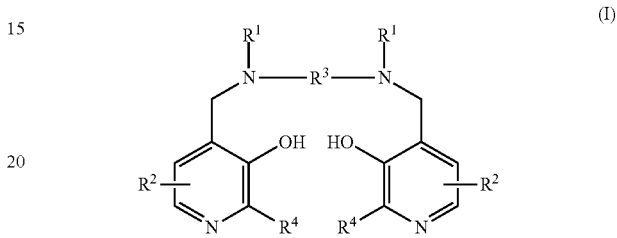

(wherein in formula I
each $R^1$ independently represents hydrogen or —$CH_2COR^5$;
$R^5$ represents hydroxy, optionally hydroxylated alkoxy, amino or alkylamido;
each $R^2$ independently represents a group $XYR^6$;
X represents a bond, or a $C_{1-3}$ alkylene or oxoalkylene group optionally substituted by a group $R^7$;
Y represents a bond, an oxygen atom or a group $NR^6$;
$R^6$ is a hydrogen atom, a hydroxyl group, a group $COOR^8$, a group $OP(O)(OR^8)R^7$, a group $OP(O)(OM)R^7$ or an alkyl, alkenyl, cycloalkyl, aryl or aralkyl group optionally substituted by one or more groups selected from $COOR^8$, $CONR^8_2$, $NR^8_2$, $OR^8$, =$NR^8$, =O, $OP(O)(OR^8)R^7$, $OP(O)(OM)R^7$ and $OSO_3M$;
$R^7$ is OM, hydroxy, an optionally hydroxylated, optionally alkoxylated alkyl or aminoalkyl group;
$R^8$ is a hydrogen atom, or an optionally hydroxylated; optionally alkoxylated alkyl group;
M is a hydrogen atom or one equivalent of a physiologically tolerable cation, e.g. an alkali or alkaline earth cation (e.g. $Na^+$), an ammonium ion or an organic amine cation, such as a meglumine ion;
$R^3$ represents a $C_{1-8}$ alkylene group, preferably a $C_{1-6}$, e.g. a $C_{2-4}$ alkylene group, a 1,2-cycloalkylene group, or a 1,2-arylene group; and
each $R^4$ independently represents hydrogen or $C_{1-3}$ alkyl).

As used herein the terms "alkyl" and "alkylene" include both straight-chained and branched, saturated and unsaturated hydrocarbons. The term "1,2-cycloalkylene" includes both cis and trans cycloalkylene groups, and alkyl substituted cycloalkylene groups having from 5-8 carbon atoms. The term "1,2-arylene" includes phenyl and napthyl groups and alkyl substituted derivatives thereof having from 6 to 10 carbon atoms.

Unless otherwise specified, any alkyl, alkylene or alkenyl moiety may conveniently contain from 1 to 20, preferably 1-8, more preferably 1-6 and especially preferably 1-4 carbon atoms.

Cycloalkyl, aryl and aralkyl moieties may conveniently contain 3-18, preferably 5-12 and especially preferably 5-8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

Particularly preferred for the uses and methods of the invention are manganese chelates of a compound of formula II and salts thereof,

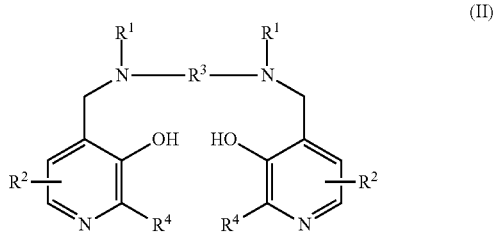

(II)

(wherein in formula II
each $R^1$ independently represents hydrogen or —$CH_2COR^5$;
$R^5$ represents hydroxy, optionally hydroxylated alkoxy, amino or alkylamido;
each $R^2$ independently represents a alkyl group (e.g. a $C_{1-6}$ alkyl group) substituted by one or more groups selected from hydroxyl, $COOR^8$, $CONR^8_2$, $NR^8_2$, $OR^8$, =$NR^8$, =O, $OP(O)(OR^8)R^7$, $OP(O)(OM)R^7$ and $OSO_3M$;
$R^7$ is OM, hydroxy, an optionally hydroxylated, optionally alkoxylated alkyl or aminoalkyl group;
$R^8$ is a hydrogen atom, or an optionally hydroxylated, optionally alkoxylated alkyl group;
M is a hydrogen atom or one equivalent of a physiologically tolerable cation, e.g. an alkali or alkaline earth cation (e.g. $Na^+$), an ammonium ion or an organic amine cation, such as a meglumine ion;
$R^3$ represents a $C_{1-8}$ alkylene group, preferably a $C_{1-6}$, e.g. a $C_{2-4}$ alkylene group; and
each $R^4$ independently represents hydrogen or $C_{1-3}$ alkyl).

In formula II, $R^5$ is preferably hydroxy. Preferably each group $R^1$ represents —$CH_2COR^5$ in which $R^5$ is hydroxy.

In further preferred compounds of formula II, $R^3$ is preferably ethylene (i.e. —$CH_2$—$CH_2$—).

In further preferred compounds each $R^4$ is $C_{1-3}$ alkyl, especially methyl.

The compounds of formula II may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Compounds in which the $R^2$ groups are identical and identically located, e.g. 6,6', are especially preferred.

In the compounds of formula II, $R^2$ is preferably a $C_{1-4}$, e.g. $C_{1-2}$ alkyl group. More preferably $R^2$ is $C_1$. Preferred substituents on $R^2$ are hydroxyl, $OP(O)(OR^8)R^7$ and $OP(O)(OM)R^7$. $R^7$ is preferably a hydroxyl group or OM. $R^8$ is preferably hydrogen.

Particularly preferred identities for group $R^2$ include $CH_2OP(O)(OM)OM$, $CH_2OP(O)(OM)OH$, $CH_2OP(O)(OH)_2$ or $CH_2OH$ groups.

Compounds of formula II in which $R^3$ is ethylene and $R^2$ has any of the identities listed above are particularly preferred.

Especially preferred for use in the method of the invention is the manganese (II) chelate of N,N'-bis-(pyridoxal-5-phosphate)-ethylenediamine-N,N'-diacetic acid (MnDPDP).

MnDPDP is also known as manganese (II) N,N'-dipyridoxyl-ethylenediamine-N,N'-diacetate-5,5'-bis(phosphate) and as mangafodipir trisodium.

Also preferred for use in the method of the invention is the manganese (II) chelate of N,N'-dipyridoxyl-ethylenediamine-N,N'-diacetic acid (MnPLED). MnPLED is also known as manganese (II) N,N-dipyridoxyl-ethylenediamine-N,N'-diacetate.

Also preferred is the manganese (II) chelate of N-pyridoxyl, N'-(pyridoxyl-5-phosphate)-ethylenediamine-N—N'-diacetic acid (MnDPMP). MnDPMP is also known as manganese (II) N,N'-dipyridoxyl-ethylenediamine-N,N'-diacetate-5-phosphate.

As hereinbefore described, the methods and uses of the invention are based on the finding that whilst both viable and non viable myocardial tissue take up manganese for a short time after administration of a manganese contrast agent such as MnDPDP, only viable cells continue to take up manganese ions over time. Hence the final amount of manganese present in a cell after a certain period of time following administration of the contrast agent provides a measure of the level of cell viability/function.

A most surprising finding is that whilst MnDPDP and its metabolites, MnDPMP and MnPLED, all result in accumulation of $Mn^{2+}$ ions in the myocardium, they do so differently. It is thought that this may be because both living and necrotic tissue uptake $Mn^{2+}$ that is produced by early transmetallation, whereas only viable cells uptake $Mn^{2+}$ in the form of MnDPMP or MnPLED or produced by delayed transmetallation of these agents.

MnDPMP and MnPLED are therefore believed to facilitate the most accurate determination of tissue viability/function. When these agents are used, very little, if any, uptake of manganese is believed to occur in necrotic tissue, therefore the highest levels of contrast can be obtained. MnDPMP and MnPLED are therefore preferred contrast agents in the uses and methods of the invention. MnDPMP is particularly preferred as it has higher water solubility than MnPLED.

If not all of the labile hydrogens of the chelates are substituted by the complexed metal ion, biotolerability and/or solubility of the chelate may be increased by substituting the remaining labile hydrogen atoms with physiologically biocompatible cations of inorganic and/or organic bases or amino acids. Examples of suitable inorganic cations include $Li^+$, $K^+$, $Na^+$ and especially $Ca^{2+}$. Suitable organic cations include ammonium, substituted ammonium, ethanolamine, diethanolamine, morpholine, glucamine, N,N,-dimethyl glucamine, lysine, arginine or ornithine.

The compounds for use in the method of the invention may be commercially available (e.g. from GE Healthcare) or may be prepared by procedures known in the art. Suitable methods for preparing the polyaminopolycarboxylic acid based chelating agents are described in EP-A-299795, EP-A-71564, DE-A-3401052, EP-A-203962 and EP-A-436579.

In preparing the dipyridoxyl compounds, the compound PLED may be used as a starting material and may be appropriately derivatised using conventional procedures to obtain the compounds of formula I. Suitable methods for preparing the compounds of formula I are described for example in EP-A-290047. Alternatively the compounds of formula I may be prepared by reacting the corresponding pyridoxal compound with an alkylene diamine according to the procedure for making PLED described by Taliaferro (Inorg. Chem. 23:1183-1192, 1984).

The manganese chelates for use in accordance with the invention may be formed by conventional procedures known in the art. In general, such processes involve dissolving or suspending a metal oxide or metal salt (e.g. nitrate, chloride or sulfate) in water or a lower alcohol such as methanol, ethanol, or isopropanol. To this solution or suspension is added an equimolar amount of the chelating agent in water or a lower alcohol and the mixture is stirred, if necessary with heating moderately or to the boiling point, until the reaction is completed. If the chelate salt formed is insoluble in the solvent used, the reaction product is isolated by filtering. If it is soluble, the reaction product is isolated by evaporating to dryness, e.g. by spray drying or lyophilising.

If acid groups such as the phosphoric acid groups are still present in the resulting chelate, it is advantageous to convert the acidic chelate salt into a neutral chelate salt by reaction with inorganic and/or organic bases or amino acids, which form physiologically acceptable cations, and to isolate them. The carboxylic and phosphoric acid groups of the chelating agents can also be neutralised by esterification to prepare carboxylate and phosphate esters. Such esters can be prepared from the corresponding alcohols by conventional procedures known in the art. Suitable esters include, for example, esters of straight-chained or branched alcohols having from 1 to 18 carbon atoms, mono and polyhydric alkyl amino alcohols having from 1 to 18 carbon atoms, preferably having from 1 to 6 carbons, such as serinol or diethanolamine, and polyhydric alcohols having from 1 to 18 carbon atoms, such as ethylene glycol or glycerol.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

In the methods and uses of the invention, the contrast agents are preferably formulated into pharmaceutical compositions in a conventional manner, e.g. with one or more physiologically acceptable carriers or diluents. Preferred compositions for the methods and uses of the invention are in a form suitable for injection or infusion directly or after dispersion in or dilution with a physiologically acceptable carrier medium, e.g. water for injections. Thus although the contrast agents may be in a form such as a powder, solutions, suspensions and dispersions in a physiologically acceptable carrier is generally preferred.

The compositions employed in the uses and methods of the invention, e.g. intravenous solutions, should be sterile and free from physiologically unacceptable agents, and should preferably have low osmolality to minimize irritation or other adverse effects upon administration, and thus the contrast medium should preferably be isotonic or slightly hypertonic. Suitable carriers or diluents therefore include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405 1412 and 1461 1487 (1975) and The National Formulary XIV, 14th ed. Washington: American Pharmaceutical Association (1975).

The contrast agents may be formulated for administration in a manner well-known to those skilled in the art. For example, the compounds, optionally with the addition of pharmaceutically acceptable excipients, may be suspended or dissolved in an aqueous medium, with the resulting solution or suspension then being sterilized. Formulation aids (e.g. stabilizers, antioxidants, osmolality adjusting agents, buffers, pH adjusting agents, preservatives, antimicrobial agents, etc) and/or additives may also be included. Representative examples of suitable additives include physiologically biocompatible buffers (e.g. DTPA or DTPA bisamide), calcium chelate complexes (e.g. calcium DTPA salts, calcium DTPA-bisamide salts or NaCaDTPA bisamide) or additions (e.g. 1 to 50 mole percent) of calcium or sodium salts (e.g. calcium chloride, calcium ascorbate, calcium gluconate or calcium lactate).

For effective uptake by the calcium channels in the cardiomycytes, the manganese is preferably in the state $Mn^{2+}$. To inhibit oxidation to $Mn^{3+}$, the compositions employed in the uses and methods of the invention will preferably contain an antioxidant, e.g. ascorbic acid or a reducing sugar.

The concentration of the compounds of the invention in the compositions used for MRI will vary depending on several factors including the nature of the compound, the nature of the composition and the type of imaging to be done. Preferably, however, concentration ranges of 0.001 to 1 mmol/ml, more preferably 0.005 to 0.1 mmol/ml, still more preferably 0.01 to 0.05 mmol/ml, e.g. about 0.01 mmol/ml compound is used.

Suitable compositions for application in the methods and uses of the invention may be available commercially. A solution of MnDPDP is, for example, available from GE Healthcare under the tradename TESLASCAN.

In the methods and uses of the invention, clinically acceptable doses of manganese are used. Conveniently, the compounds as hereinbefore described may be administered at a dosage of from 0.5 to 40 mmol/kg body weight, more preferably 1 to 20 ƒmol/kg body weight, still more preferably 2 to 12 µmol/kg body weight, e.g. about 5 to 10 µmol/kg body weight. Preferably the compounds are administered by bolus injection or infusion into the systemic vasculature. Infusion is preferred.

In preferred methods and uses of the invention, the manganese contrast agent is administered over a short period of time, e.g. within 1 to 30 minutes, more preferably 2 to 20 minutes, still more preferably 5 to 10 minutes. The preferred rate of administration is therefore in the range 0.01-1 ml/kg/minute, still more preferably 0.02-0.5 ml/kg/minute. Such administration rates are readily achievable using conventional delivery equipment.

Administration of the manganese contrast agent to the individual may occur outside of the magnetic field used for MRI or may occur inside the magnetic field. Generally, however, it is preferred if administration occurs outside of the magnetic field.

When administration occurs outside of the magnetic field used for MRI, the MRI is preferably carried out within 0.5 to 6 hours, preferably 1 to 4 hours, e.g. 1.5 to 3 hours thereafter. When administration is conducted inside of the magnetic field used for MRI, the MRI is carried out intermittently before, during and/or thereafter (e.g. preferably within 30 to 60 minutes thereafter).

In the methods and uses of the invention, SI and/or $R_1$ measurements are preferably used to provide a quantitative measurement of cell viability/function. Although SI and $R_1$ measurements are well described in the MRI literature, as far as the applicant is aware, there has been no prior publication of a method for graded or quantitative measurement of cell viability/function and thus for cardiac remodelling. This can now be achieved by use of an intracellular contrast agent as described herein. As will be clear from the examples hereinafter described, $R_1$ changes are only modestly detectable without manganese contrast agent, but are greatly enhanced with manganese.

Thus, in the methods and uses of the invention, a quantitative measurement of myocardial viability/function is preferably assessed by determining the amount of intracellular manganese in the myocardium, e.g. by determining the MRI SI or by determining $R_1$. In preferred methods of the invention the amount of intracellular manganese is assessed by determining $R_1$. In particular, it is the left ventricle of the heart which is imaged. More specifically, the invention allows the differentiated Mn uptake and $R_1$ change throughout the entire left ventricle to be detected and that result correlated to the presence or absence cardiac remodelling.

In a particularly preferred method or use of the invention, the myocardium is divided into a number of transmural sectors (e.g. 5 to 50, more preferably about 10 to 30 sectors, still more preferably 24 sectors). Alternatively regions of interest (ROD are chosen from different layers of the myocardium. Both approaches make it possible to create composite distribution plots of $R_1$ thus revealing the differentiated distribution of magnetized water protons in the imaged pixels.

A reference SI and/or $R_1$ is preferably determined without contrast agent for each sector or layer. During and/or following administration of the manganese contrast agent, a number of SI measurements for each sector or layer are taken over time (e.g. every 1 to 30 seconds, more preferably every 5 to 20 seconds, still more preferably about every 10 seconds). Imaging is preferably continued in this way for 20 minutes to 2 hours, preferably 30 minutes to 1 hour, e.g. about 45 minutes. A total of 100 to 500 (e.g. 250 to 400) measurements may therefore be taken for a selected slice of myocardium and thus of each sector or layer. Alternatively images can be produced at fewer time points, e.g. at 5-10 minute intervals over 30-45 minutes. Both approaches enable a continuous or semi-continuous determination of $Mn^{2+}$ uptake.

With repeated examinations at intervals of weeks to months after AMI, the processes of remodelling and/or their responses to therapy can be followed.

In a preferred method or use according to the present invention, each of the SI measurements determined as described above are fitted to the signal equation [1] to obtain an estimate for $R_1$:

$$S = \left| \Omega M_0 \sin\alpha \left[ (1 - 2e^{(-R_1 TI)})a^{n-1} + \frac{b(1 - a^{n-1})}{(1-a)} \right] \right| \quad [1]$$

In this equation S is the signal intensity, $\Omega$ is a constant dependent on receiver gain, instrumental conditions and $T_2^*$ decay (which is a constant with the short TEs used), $M_0$ is the fully relaxed longitudinal magnetization, $\alpha$ is the angle of the RF pulse used, TI is the inversion time measured to the start of the $\alpha$-RF-pulse chain, n is the number of $\alpha$-pulses until the centre of K-space, TR is the time interval between two $\alpha$-pulses in the pulse chain, $a = (\cos\alpha \exp(-R_1 TR))$ and $b = (1-\exp(-R_1 TR))$. Any conventional fitting procedure may be used, e.g. a simplex search method and a least-squares cost function. Fitting preferably yields values for $R_1$ and $\Omega M_0$. Separate values for each sector may then be calculated, e.g. for both the reference SI measurement and the final SI measurement to determine $R_1$ at each stage as well as $\Delta R_1$, the $R_1$ value at 1 hour minus the reference $R_1$ value. The final $R_1$ values provide a measure of viability/function and are preferably plotted as a $R_1$ map. Several maps may be established for a patient over a period of time (e.g. 2 weeks to 6 months) to monitor cardiac remodelling.

In some preferred methods and uses of the invention, the $\Delta R_1$ values are analysed to identify regions of interest (ROIs). Typically ROIs will cover those areas where a suspected infarct has occurred. The SIs determined over time are then preferably extracted for those ROIs and converted to temporal $R_1$ changes. This may be used to confirm whether the ROI comprises viable tissue.

The MRI employed in the methods and uses of the invention may be carried out using conventional MRI equipment. Inversion techniques or saturation techniques, especially inversion techniques based on the Look-Locker MRI methods known in the art are preferably used.

The methods and uses of the invention may be employed on any individual. By the term "individual" is meant herein any human or non-human being. Preferred individuals for application of the methods and uses of the invention are humans. Although the methods and uses may be utilised on individuals who have not suffered a AMI, particularly preferred individuals are those having suffered a prior AMI. In such individuals the methods and uses of the invention may be used to detect cardiac remodelling.

BRIEF DESCRIPTION OF THE DRAWINGS

The method of the invention will now be illustrated further by way of examples with particular reference to certain non-limiting embodiments and to the accompanying figures wherein:

FIG. 1 shows the hypothesised metabolic breakdown of MnDPDP in vivo.

FIG. 2 shows the changes in signal intensity (SI) in the myocardium (black) and blood (grey) in a healthy individual following administration of Teslascan (5 μmol/kg over 5 minutes (a) and over 30 minutes (b))

FIG. 3 shows temporal $R_1$ changes from blood (dotted line), suspected myocardial infarct (grey line) and the remote region (black line) in a patient with a fully developed infarct.

FIG. 4 shows temporal $R_1$ changes from blood (dotted line), suspected infarcted region (grey line) and a remote region (black line) in a patient wherein treatment by PCI at onset of infarction resulted in myocardial salvage.

FIG. 5 shows $R_1$ maps of short axis slices from a patient treated with PCI but with a fully developed infarct.

FIG. 6 shows $R_1$ maps of short axis slices from a patient wherein treatment by PCI at onset of infarction resulted in myocardial salvage

EXAMPLES

Magnetic Resonance Imaging

MR-examinations were carried out in 10 patients 3-12 weeks following an acute coronary episode with onset of acute myocardial infarction (AMI). All patients were revascularized by percutaneous coronary intervention (PCI) immediately after admission to hospital for AMI.

Examinations were performed on a Siemens Magnetom Symphony 1.5 Tesla scanner with Quantum gradients (Software Version: Syngo 2002B, VA21B. Gradient strength: 30 mT/m.). Recordings were done with a body phase-array surface coil. An electrocardiographic (ECG) signal was used for heart rate monitoring and sequence triggering.

Steady-state free precession (true-FISP) cine short axis slices were made covering the ventricular length. Each slice was acquired during one breath-hold, with a slice thickness of 8 millimeters and slice separation of 10 millimeters. Based on examination of the short axis cine images for signs of impaired wall motion and systolic wall thickening, one slice was selected in each patient for imaging of contrast enhancement. The slice location parameters from this slice of interest (SOI) were copied and used through the remaining MRI examinations.

Pre-contrast myocardial and blood $R_1$-measurements in the SOI were performed through a series of 20 images using an inversion recovery (IR) turbo-FLASH (fast low-angle shot) sequence with subsequently increasing inversion-times ($T_1$). The sequence used a nonselective 180 degree inversion pulse followed by an ultra fast FLASH sequence, consisting of repetitive low-angle slice selective α-pulses with gradient echoes generated in between the α-pulses. The inversion times used spanned from 90 to 5000 ms. The parameter settings were: bandwidth: 1000 Hz/pixel, echo spacing (TR): 1.9 ms, TE: 1.06 ms, field of view: 380 mm, slice thickness: 8 mm, α-flip angle: 12 degrees and a phase partial Fourier of 6/8.

After the initial $R_1$-measurement, the MR-scanner was set to record a series of IR-images with the same parameter settings as used for the $R_1$-measurements, but with a fixed inversion time of 400 ms.

After 10 reference images, patients received 5 µmol MnDPDP per kg body weight of a 0.01 mmol/ml solution (Teslascan, Amersham) as a peripheral intravenous infusion over five minutes. A total of 300-350 IR images were acquired over of 40-45 minutes. Throughout these infusion series, a time interval of 7-8 seconds was maintained between individual images.

Then imaging, for the purpose of visualization of infarcted regions, was performed. Two $T_1$ weighted ECG-gated segmented sequences were tried out: an IR turbo-FLASH sequence and an IR true-FISP sequence with the possibility of phase sensitive reconstruction. In either case, individualized inversion times were used, depending on heart rate and ability for breath holds.

Finally, a second $R_1$-measurement consisting of 20 IR turbo-FLASH images over five min was performed one hour after the start of the contrast infusion. $R_1$ analyses $R_1$ Analysis The images for the $R_1$ measurements were analyzed using software written in Matlab version 6.5 (MathWorks, USA) and the inner and outer borders of the LV wall were drawn manually in each single slice. The outlined myocardium was then divided into 24 sectors. The signal intensity was extracted and analyzed separately for each sector. The signal equation was fitted to the data from the sectors to obtain an estimate of $R_1$.

$$S = \left| \Omega M_0 \sin\alpha \left[ (1 - 2e^{(-R_1 TI)})a^{n-1} + \frac{b(1-a^{n-1})}{(1-a)} \right] \right| \quad [1]$$

In this equation, S is the signal intensity, Ω is a constant dependent on receiver gain, instrumental conditions and $T_2^*$ decay (which is a constant with the short TEs used), $M_0$ is the fully relaxed longitudinal magnetization, α is the angle of the RF pulse used, TI is the inversion time measured to the start of the α-RF-pulse chain, n is the number of α-pulses until the centre of K-space, TR is the time interval between two α-pulses in the pulse chain, a=(cos α exp(−$R_1$TR)) and b=(1−exp(−$R_1$TR)). The fitting was performed with two variables: $R_1$ and the product of $\Omega M_0$. These two variables were optimized using a simplex search method and a least-squares cost function.

Separate $R_1$ values were calculated for each of the 24 sectors for both the reference $R_1$ measurements and the measurements after one hour. A $\Delta R_1$ value for each sector was calculated as the one-hour $R_1$ value minus the reference value.

Temporal $R_1$ Changes

Temporal $R_1$ changes following contrast infusion were created by combining each patient's reference $R_1$ measurements with the patient's infusion series. The images were analysed together in software written in Matlab. Based upon the $\Delta R_1$ values, two small ROIs (5 to 8 pixels in size) were drawn centrally in the LV wall. One ROI was placed in the centre of the assumed infarct region and one in a remote region supplied by a different coronary artery. A third ROI was placed in blood in the LV cavity, and given a diameter of approximately half the inner LV diameter. Each ROI was drawn in the first image and copied through all images of the $R_1$-measurement as well as through the infusion series. The ROIs were then manually adjusted for respiratory motions. Signal intensities were extracted and pre-contrast $R_1$-measurements were made though Equation 1. The estimated $\Omega M_0$ products were then, by equation 1, used to convert the changes in signal intensities following the infusions into temporal $R_1$ changes Results Infusion and Post Infusion MRI Kinetics FIGS. 3 and 4 show the results of temporal $R_1$ determination in two of the ten patients. FIG. 3 shows the results obtained from a patient treated with PCI but who still developed a full infarct as confirmed by previous history and now also by $T_1$ weighted MRI. During the infusion of Teslascan (0-5 min) there is an early Mn uptake not only in the remote and viable region but also in the infarcted area, and after the infusion there is a late Mn uptake in the remote region but not in the infarcted area. The absence of late uptake in the infarct region indicates that it contains scar tissue without viable myocardial cells.

In contrast, FIG. 4 shows the results obtained from a patient who received treatment by PCI much earlier after the onset of infarction. In this patient early intervention resulted in myocardial salvage as confirmed by clinical parameters and now also by $T_3$ weighted MRI. During the infusion of Teslascan (0-5 min), similar uptake profiles with both an early and a late Mn uptake were observed both in the previous area at risk (infarcted region) as in the remote region. This indicates that all cells are viable.

These observations in the two patients indicate two phases of $Mn^{2+}$ ion uptake and that different manganese agents were responsible: an early uptake during the 5 min period of infusion occurred from the mother substance MnDPDP; and a late uptake occurred in the postinfusion period after conversion of MnDPDP to its two metabolites MnDPMP and MnPLED. Surprisingly, the observations show that whereas an early uptake with MnDPDP indicates viability plus perfusion of the myocardium, a late uptake specifically indicates viability. MnDPDP is therefore a viability plus perfusion marker, whilst MnDPMP and MnPLED are pure viability markers.

$R_1$ Mapping of Short Axis Slices $R_1$ maps in short axis slices of the heart covering the previous areas of developed or suspected infarctions were prepared for the same two patients and are shown in FIGS. 5 and 6. These show that much more graded information can be obtained by the uses and methods of the invention. Prior to infusion of Teslascan hardly any differences can be observed in the $R_1$ values between sectors, but 45 min thereafter a much more marked heterogeneity appears.

In the patient with a persistent post infarction defect (FIG. 5), in the first background MR images the $R_1$'s are 0.80 s$^{-1}$ and 0.95 s$^{-1}$ in the infarcted vs the remote zones, i.e. a difference in $R_1$ of ~0.15 s$^{-1}$ In the manganese enhanced MR images the respective $R_1$'s are 0.95 s$^{-1}$ and 1.35 s$^{-1}$, i.e. a difference in $R_1$ of ~0.40 s$^{-1}$. This result may be explained by the remote regions late uptake of manganese. Surprisingly and more importantly, however, there is a gradual difference from the infarct zone (0.95 s$^{-1}$): to the border zone (1.10 s$^{-1}$); then to large intermediary zones (1.20 s$^{-1}$); and finally into the remote and major zone (1.35 s$^{-1}$).

In the patient with myocardial salvage (FIG. 6), there is hardly any differences between transmural sectors before or after contrast. Thus homegeneity is maintained and there is an average elevation of $R_1$ of ~0.40 s$^{-1}$ as expected for normal myocardium after Mn infusion. The intersector variation is within ~0.05 to 0.10 s$^{-1}$.

These results from $R_1$ mapping demonstrates detectable regional alterations in tissue relaxation and thus in tissue Mn uptake/retention during recovery from a fully developed AMI. This is consistent with postinfarct cardiac remodelling, here for the first time demonstrated with intracellular paramagnetic Mn ions reflecting either the overall number of live cardiac cells and/or the state of function of these cells.

In the patient with the persistent infarct and scar tissue the $R_1$ findings were consistent with a reduced LV ejection fraction (49%) and indicated a need for therapy in order to delay the development of an overt HF. In the other patient without signs of remodelling of the left ventricle and a normal LV ejection fraction (71%) there was no need for such specific therapy.

The invention claimed is:

1. A method of diagnosing cardiac remodeling and likelihood of arrhythmias and of heart failure, by a single examination in a human individual weeks to months after said individual has suffered an acute myocardial infarction, said method consisting of four consecutive steps:
   (i) administering intravenously to said individual a manganese contrast agent capable of releasing manganese ions or an intact manganese contrast agent, or pharmaceutically acceptable salts thereof, for enabling uptake of manganese in cardiomyocytes of said individual;
   (ii) thereafter subjecting said individual to one MRI procedure measuring a longitudinal relaxation rate, $R_1$, or its reciprocal a longitudinal relaxation time, $T_1$, throughout sectors and layers of the myocardium and expressing the measured $R_1$ or $T_1$ values in maps of said myocardium;
   (iii) detecting the presence of a continuous gradient of $R_1$ or $T_1$ in the myocardium from a site of infarction to a region remote from said site, wherein the $R_1$ values correlate positively and the $T_1$ values correlate negatively to the function and viability of cardiomyocytes; and
   (iv) diagnosing the individual with cardiac remodeling and likelihood of arrhythmias and heart failure when the presence of said continuous gradient in $R_1$ or $T_1$ is detected;
   wherein the step (iii) comprises:
      (a) determining whether the $R_1$ values of the sectors or layers exhibit the continuous gradient from subnormal values at a site of infarction to supernormal values at a region remote from said site, wherein the $R_1$ values correlate positively to the function and viability of cardiomyocytes; or
      (b) determining whether the $T_1$ values of the sectors or layers exhibit the continuous gradient from supernormal values at a site of infarction to subnormal values at a region remote from said site, wherein the $T_1$ values correlate negatively to the function and viability of cardiomyocytes.

2. The method as claimed in claim 1 wherein said manganese contrast agent capable of releasing manganese ions is a manganese ion releasing chelate.

3. The method as claimed in claim 2 wherein said manganese ion releasing chelate has a Ka value in the range of $10^7$ to $10^{25}$.

4. The method as claimed in claim 2, wherein said manganese ion releasing chelate is a dipyridoxyl compound.

5. The method as claimed in claim 2, wherein said manganese ion releasing chelate is a compound of formula II and salts thereof,

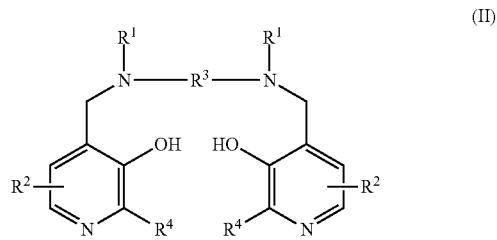

wherein in formula II
each $R^1$ independently represents hydrogen or —CH$_2$COR$^5$;
$R^5$ represents hydroxy, optionally hydroxylated alkoxy, amino or alkylamido;
each $R^2$ independently represents an alkyl group substituted by one or more groups selected from hydroxyl, COOR$^8$, CONR$^8$$_2$, NR$^8$$_2$, OR$^8$, =NR$^8$, =O, OP(O)(OR$^8$)R$^7$, OP(O)(OM)R$^7$ and OSO$_3$M;
$R^7$ is OM, hydroxy, an optionally hydroxylated, optionally alkoxylated alkyl or aminoalkyl group;
$R^8$ is a hydrogen atom, or an optionally hydroxylated, optionally alkoxylated alkyl group;
M is a hydrogen atom or one equivalent of a physiologically tolerable cation;
$R^3$ represents a C$_{1-8}$ alkylene group; and
each $R^4$ independently represents hydrogen or C$_{1-3}$ alkyl.

6. The method as claimed in claim 5, wherein each $R^2$ independently represents a C$_{1-6}$ alkyl group substituted by one or more groups selected from the group consisting of hydroxyl, COOR$^8$, CONR$^8$$_2$, NR$^8$$_2$, OR$^8$, =NR$^8$, =O, OP(O)(OR$^8$)R$^7$, OP(O)(OM)R$^7$ and OSO$_3$M.

7. The method as claimed in claim 5, wherein the physiologically tolerable cation is an alkali or alkaline earth cation, an ammonium ion or an organic amine cation.

8. The method as claimed in claim 5, wherein $R^3$ represents a C$_{1-6}$ alkylene group.

9. The method as claimed in claim 5, wherein $R^3$ represents a C$_{2-4}$ alkylene group.

10. The method as claimed in claim 2, wherein said manganese ion releasing chelate has a Ka value in the range of $10^9$ to $10^{24}$.

11. The method as claimed in claim 2, wherein said manganese ion releasing chelate has a Ka value in the range of $10^{10}$ to $10^{23}$.

12. The method as claimed in claim 2, wherein said manganese ion releasing chelate has a Ka value in the range of $10^{12}$ to $10^{22}$.

13. The method as claimed in claim 1, wherein said manganese contrast agent capable of releasing manganese ions is selected from the group consisting of MnDPDP, MnDPMP and MnPLED.

14. The method as claimed in claim 1, wherein said manganese contrast agent capable of releasing manganese ions is selected from the group consisting of MnDPMP and MnPLED.

15. The method as claimed in claim 1, wherein said manganese contrast agent capable of releasing manganese ions is MnDPDP.

16. The method as claimed in claim 1, wherein said manganese contrast agent capable of releasing manganese ions or an intact manganese contrast agent, or pharmaceutically acceptable salts thereof is administered in a dose of 0.5 to 40 μmol/kg bodyweight.

17. The method as claimed in claim 16, wherein the dose is 1 to 20 μmol/kg bodyweight.

18. The method as claimed in claim 16, wherein the dose is 2 to 10 μmol/kg bodyweight.

19. The method as claimed in claim 1, wherein said manganese contrast agent capable of releasing manganese ions or an intact manganese contrast agent, or pharmaceutically acceptable salts thereof is administered by intravenous infusion over 1 to 30 minutes.

20. The method as claimed in claim 19, wherein the intravenous infusion is over 2 to 20 minutes.

21. The method as claimed in claim 19, wherein the intravenous infusion is over 5 to 10 minutes.

22. The method as claimed in claim 1, wherein said administration of said manganese contrast agent capable of releasing manganese ions or an intact manganese contrast agent, or pharmaceutically acceptable salts thereof is conducted outside of the magnetic field used for said MRI procedure and MRI is carried out within 0.5 to 6 hours thereafter.

23. The method as claimed in claim 22, wherein the MRI is carried out within 1 to 4 hours thereafter.

24. The method as claimed in claim 22, wherein the MRI is carried out within 1.5 to 3 hours thereafter.

25. The method as claimed in claim 22, wherein the MRI is carried out within 30 to 60 minutes thereafter.

26. The method as claimed in claim 1, wherein said administration of said manganese contrast agent capable of releasing manganese ions or an intact manganese contrast agent, or pharmaceutically acceptable salts thereof is conducted inside of the magnetic field used for said MRI procedure and MRI is carried out intermittently before, during and/or thereafter.

27. The method as claimed in claim 1 wherein said manganese contrast agent capable of releasing manganese ions is administered to said individual.

28. The method of claim 1, wherein the number of sectors of the myocardium is 5 to 50.

29. A method of diagnosing cardiac remodeling and likelihood of arrhythmias and of heart failure, by a single examination in a human individual weeks to months after said individual has suffered an acute myocardial infarction, said method consisting of four consecutive steps:
(i) administering intravenously to said individual a manganese contrast agent capable of releasing manganese ions or an intact manganese contrast agent, or pharmaceutically acceptable salts thereof, for enabling uptake of manganese in cardiomyocytes of said individual;
(ii) thereafter subjecting said individual to one MRI procedure measuring a signal intensity in $R_1$ weighted images throughout sectors and layers of the myocardium and expressing the measured signal intensity in images of said myocardium;
(iii) detecting the presence of a continuous gradient of signal intensity in the myocardium from a site of infarction to a region remote from said site, wherein the signal intensity correlates positively to the function and viability of cardiomyocytes; and
(iv) diagnosing the individual with cardiac remodeling and likelihood of arrhythmias and heart failure when the presence of said continuous gradient in signal intensity is detected;
wherein the step (iii) comprises determining whether the signal intensity of the sectors or layers exhibit the continuous gradient from subnormal values at a site of infarction to supernormal values at a region remote from said site.

30. A method of detecting a continuous gradient of a longitudinal relaxation rate or a longitudinal relaxation time in a myocardium from a site of infarction to a region remote from said site in a human individual in a single examination, said method consisting of:
(i) administering intravenously over 1 to 30 minutes a dose of 0.5 to 40 μmol/kg body weight of a chelated manganese contrast agent capable of releasing manganese ions with a Ka value in the range of $10^7$ to $10^{25}$, or a pharmaceutically acceptable salt thereof, to said individual weeks to months after said individual has suffered an acute myocardial infarction;
(ii) subjecting said individual to one MRI procedure measuring a longitudinal relaxation rate, $R_1$, or its reciprocal the longitudinal relaxation time, $T_1$, throughout sectors and layers of the myocardium of said individual and expressing the measured $R_1$ or $T_1$ values in maps of said myocardium;
(iii) dividing the maps of $R_1$ or $T_1$ into transmural sectors or layers to create a composite distribution plot of $R_1$ or $T_1$;
(iv) detecting the presence of the continuous gradient of the $R_1$ or $T_1$ values of the sectors or layers in the myocardium from a site of infarction to a region remote from said site, wherein the $R_1$ values correlate positively or the $T_1$ values correlate negatively to the function and viability of cardiomyocytes; and
(v) diagnosing the individual with cardiac remodeling and an increased risk of arrhythmia or heart failure when the presence of said continuous gradient in $R_1$ or $T_1$ is detected;
wherein the step (iv) comprises:
(a) determining whether the $R_1$ values of the sectors or layers exhibit the continuous gradient from subnormal values at a site of infarction to supernormal values at a region remote from said site, wherein the $R_1$ values correlate positively to the function and viability of cardiomyocytes; or
(b) determining whether the $T_1$ values of the sectors or layers exhibit the continuous gradient from supernormal values at a site of infarction to subnormal values at a region remote from said site, wherein the $T_1$ values correlate negatively to the function and viability of cardiomyocytes.

31. A method of assessing the risk of arrhythmias or heart failure in an individual, examined weeks to months after suffering an acute myocardial infarction, by subjecting said individual to a single diagnostic procedure to determine the presence and extent of remodeling of myocardium, said method consisting of the following four steps:
(i) administering intravenously a manganese contrast agent capable of releasing manganese ions or an intact manganese chelate contrast agent for cardiomyocyte uptake, or a pharmaceutically acceptable salt thereof, to said individual;
(ii) subjecting said individual to an MRI procedure to determine viability and function of cardiomyocytes by measuring a longitudinal relaxation rate, $R_1$, or its reciprocal a longitudinal relaxation time, $T_1$, throughout sectors and layers of the myocardium and mapping the measured $R_1$ or $T_1$ values throughout said myocardium;
(iii) detecting remodeling of myocardium by observing a continuous gradient of $R_1$ or $T_1$ in the myocardium from a site of infarction to a region remote from said site wherein the $R_1$ values correlate positively and the $T_1$ values correlate negatively to the function and viability of cardiomyocytes; and
(iv) quantifying the extent of remodeling and the risk of arrhythmias or heart failure by measuring the continuous gradient in $R_1$ or $T_1$;
wherein the step (iii) comprises:
(a) determining whether the $R_1$ values of the sectors or layers exhibit the continuous gradient from subnormal values at a site of infarction to supernormal values at a region remote from said site, wherein the $R_1$ values correlate positively to the function and viability of cardiomyocytes; or
(b) determining whether the $T_1$ values of the sectors or layers exhibit the continuous gradient from supernormal values at a site of infarction to subnormal values at a region remote from said site, wherein the $T_1$ values correlate negatively to the function and viability of cardiomyocytes.

32. The method of claim 31, wherein the method assesses the risk of arrhythmias.

* * * * *